(12) United States Patent  
Kroll et al.

(10) Patent No.: US 7,010,358 B1
(45) Date of Patent: Mar. 7, 2006

(54) SINGLE LEAD SYSTEM FOR HIGH VOLTAGE CHF DEVICE

(75) Inventors: Mark W. Kroll, Simi Valley, CA (US); John R. Helland, Saugus, CA (US)

(73) Assignee: Pacesetter, Inc., Sylmar, CA (US)

( * ) Notice: Subject to any disclaimer, the term of this patent is extended or adjusted under 35 U.S.C. 154(b) by 237 days.

(21) Appl. No.: 10/640,242

(22) Filed: Aug. 12, 2003

(51) Int. Cl.
*A61N 1/05* (2006.01)

(52) U.S. Cl. ................................ 607/122
(58) Field of Classification Search ........ 607/119–126; 600/373–375, 17, 377
See application file for complete search history.

(56) References Cited

U.S. PATENT DOCUMENTS

| | | | |
|---|---|---|---|
| 5,129,394 A * | 7/1992 | Mehra | 607/23 |
| 5,800,465 A | 9/1998 | Thompson et al. | 607/9 |
| 6,201,994 B1 | 3/2001 | Warman et al. | 607/123 |
| 6,295,475 B1 | 9/2001 | Morgan | 607/122 |
| 6,490,489 B1 | 12/2002 | Bornzin et al. | 607/122 |
| 2002/0103523 A1 | 8/2002 | Helland et al. | 607/122 |
| 2002/0103524 A1 | 8/2002 | Bornzin et al. | 607/122 |
| 2004/0267086 A1 * | 12/2004 | Anstadt et al. | 600/17 |

FOREIGN PATENT DOCUMENTS

| | | |
|---|---|---|
| EP | 0813889 A2 | 12/1997 |
| EP | 0813889 A3 | 11/1998 |
| EP | 0919254 A2 | 6/1999 |
| EP | 0919254 A3 | 5/2000 |
| EP | 1226843 A2 | 7/2002 |
| EP | 1226843 A3 | 11/2002 |

* cited by examiner

*Primary Examiner*—George Manuel

(57) ABSTRACT

An implantable cardiac lead for use in the coronary sinus region of a heart for the treatment of congestive heart failure includes an elongated lead body having a plurality of terminals at its proximal end, an electrode assembly including a defibrillation electrode, for example, a metallic coil, and first and second pacing electrodes, the first pacing electrode being an electrode at or adjacent to the tip of the lead spaced from the defibrillation electrode and adjacent the apex of the left ventricle of the heart, the second pacing electrode including a ring electrode spaced proximally from the defibrillation electrode and adjacent the basal region of the left ventricle of the heart, and a plurality of conductors connecting each electrode to a respective one of the terminals at the proximal end of the lead body.

15 Claims, 3 Drawing Sheets

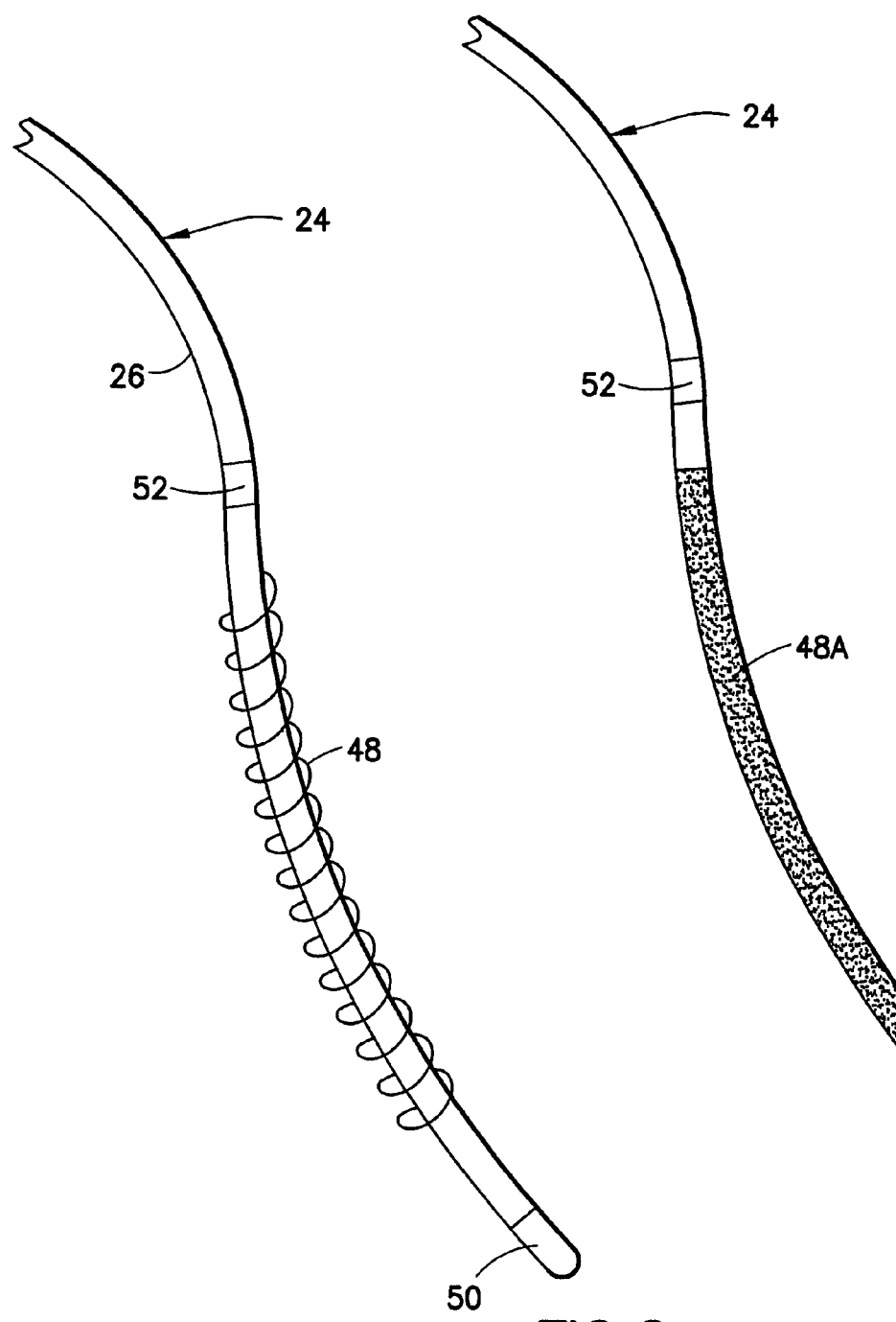

SINGLE LEAD SYSTEM FOR HIGH VOLTAGE CHF DEVICE

FIELD OF THE INVENTION

The present invention relates generally to lead assemblies for connecting implantable medical devices with selected body tissue to be stimulated by such devices, and more particularly, to such lead assemblies in the form of a high voltage system designed for treating congestive heart failure (CHF) with a single lead that paces both the apex and the base of the heart and has an intermediate defibrillation electrode for appropriate defibrillation.

BACKGROUND OF THE INVENTION

Implantable cardiac stimulation devices are well known in the art. Such devices may include, for example, implantable cardiac pacemakers and defibrillators. The devices are generally implanted in a pectoral region of the chest beneath the skin of a patient within what is known as a subcutaneous pocket. The implantable devices generally function in association with one or more electrode carrying leads which are implanted within the heart. The electrodes are usually positioned within the right side of the heart, either within the right ventricle or right atrium, or both, for making electrical contact with their respective heart chamber. Conductors within the leads couple the electrodes to the device to enable the device to sense cardiac electrical activity and deliver the desired therapy.

Traditionally, therapy delivery had been limited to the venous, or right side of the heart. The reason for this is that implanted electrodes can cause blood clot formation in some patients. If a blood clot were released arterially from the heart left side, as for example the left ventricle, it could pass directly to the brain potentially resulting in a paralyzing or fatal stroke. However, a blood clot released from the right heart, as from the right ventricle, would pass into the lungs where the filtering action of the lungs would prevent a fatal or debilitating embolism in the brain.

Recently, new lead structures and methods have been proposed and even practiced for delivering cardiac rhythm management therapy to the left heart. These lead structures and methods avoid direct electrode placement within the left atrium and left ventricle of the heart by lead implantation within the coronary sinus region of the heart. As used herein, the phrase "coronary sinus region" refers to the venous vasculature of the left ventricle, including any portions of the coronary sinus, great cardiac vein, left marginal vein, left posterior ventricular vein, middle cardiac vein, and/or small cardiac vein or any other cardiac vein accessible by the coronary sinus.

It has been demonstrated that electrodes placed in the coronary sinus region of the heart may be used for left atrial pacing, left ventricular pacing, and cardioversion and defibrillation. These advancements enable implantable cardiac stimulation devices to address the needs of a patient population with left ventricular dysfunction and/or congestive heart failure which would benefit from left heart side pacing, either alone or in conjunction with right heart side pacing (bi-chamber pacing), and/or defibrillation. Many present CHF devices require both a lead in the left ventricle (LV) and a separate lead in the right ventricle (RV), the RV lead intended for pacing the apex or tip of the heart while the LV is for pacing the far side to obtain better synchronization. The significance of a single lead for positioning only in the left ventricle is that it is easier and less time consuming to implant only one lead rather than two and, additionally two leads can "saw" against each other where they cross in the RA (right atrium).

By pacing simultaneously from the distal, apical electrode to the proximal, basal electrode ring in the LV, a cleaner contraction is obtained, with improved cardiac output, and patients are found to have more energy. In this regard, it should be noted that the "simultaneous" stimulation is often better achieved when there is a time separation of up to 50 ms between the two sites.

Cardiac leads intended for use in providing both cardiac pacing and defibrillation in the left side of the heart via the coronary sinus region have previously been difficult to position due to the tortuous venous routes of the human anatomy. Moreover, to provide both pacing and defibrillation of both the left atrium and the left ventricle from the coronary sinus region with multiple leads employing the appropriate types of electrodes is extremely difficult given the space constraints to accommodate multiple leads in the coronary sinus region. Hence, such known implants have been too cumbersome, difficult, and time consuming to perform and likely resulted in compromised performance or system malfunction.

Typical of known implantable cardiac leads for use in the coronary sinus region of the heart are U.S. Pat. Nos. 6,295,475 to Morgan entitled "Single-Pass Atrial Ventricular Lead with Multiple Atrial Ring Electrodes and a Selective Atrial Electrode Adapter for the Coronary Sinus Region" and 6,490,489 to Bornzin et al. entitled "Implantable Cardiac Single Pass Coronary Sinus Lead for Providing Pacing and Defibrillation and Method of Manufacture", as well as U.S. Publication Nos. U.S. 2002/0103523 to Helland et al. entitled "Implantable Cardiac Coronary Sinus Lead Having a Defibrillation Electrode of Split Configuration and Method of Manufacture" and U.S. 2002/0103524 to Bornzin et al. entitled "Implantable Cardiac Single Pass Coronary Sinus Lead for Providing Pacing and Defibrillation and Method of Manufacture".

It was with knowledge of the foregoing state of the technology that the present invention has been conceived and is now reduced to practice.

SUMMARY

What is described herein is a single cardiac lead for implant in the cardiac sinus region of the heart. The lead includes all of the electrodes necessary for ventricular pacing and defibrillation from the coronary sinus region. As a result, with the lead of the present invention, the implanter seeking such combined functionality need only implant a single lead. Accordingly, an implantable cardiac lead for use in the coronary sinus region of a heart for the treatment of congestive heart failure includes an elongated lead body having a plurality of terminals at its proximal end, an electrode assembly including a defibrillation electrode, for example, a metallic coil electrode, and first and second pacing electrodes, the first pacing electrode being an electrode distally spaced from the defibrillation electrode and at or adjacent to the distal end of the lead, which is adjacent to the apex of the left ventricle of the heart, the second pacing electrode including a ring electrode spaced proximally from the defibrillation electrode and adjacent the basal region of the left ventricle of the heart, and a plurality of conductors connecting each electrode to a respective one of the terminals at the proximal end of the lead body. The defibrillation electrode includes a metallic coil and, preferably, a gold-filled silicone rubber electrode.

A primary feature, then, of the present invention is the provision of a lead assembly for connecting implantable medical devices with selected body tissue to be stimulated by such devices in the form of a high voltage system designed for treating congestive heart failure (CHF) with a single lead that paces both the apex and the base of the heart and has an intermediate defibrillation coil for appropriate defibrillation.

Another feature of the present invention is the provision of such a lead assembly that includes a defibrillation electrode and first and second pacing electrodes, the first pacing electrode being spaced from the defibrillation electrode and positioned at, or adjacent to, the distal end of the lead body adjacent the apex of the left ventricle of the heart, the second pacing electrode spaced proximally from the defibrillation electrode and adjacent the basal region of the left ventricle of the heart and including a plurality of conductors connecting each electrode to a respective one of the terminals at the proximal end of the lead body.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

BRIEF DESCRIPTION OF THE DRAWINGS

The foregoing aspects and other features of the present invention are explained in the following description, taken in connection with the accompanying drawings, wherein:

FIG. 2 is a detail elevation view illustrating the distal end of a lead system embodying the invention;

FIG. 3 is a detail elevation view similar to FIG. 2 and showing another embodiment of the lead.

DETAILED DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
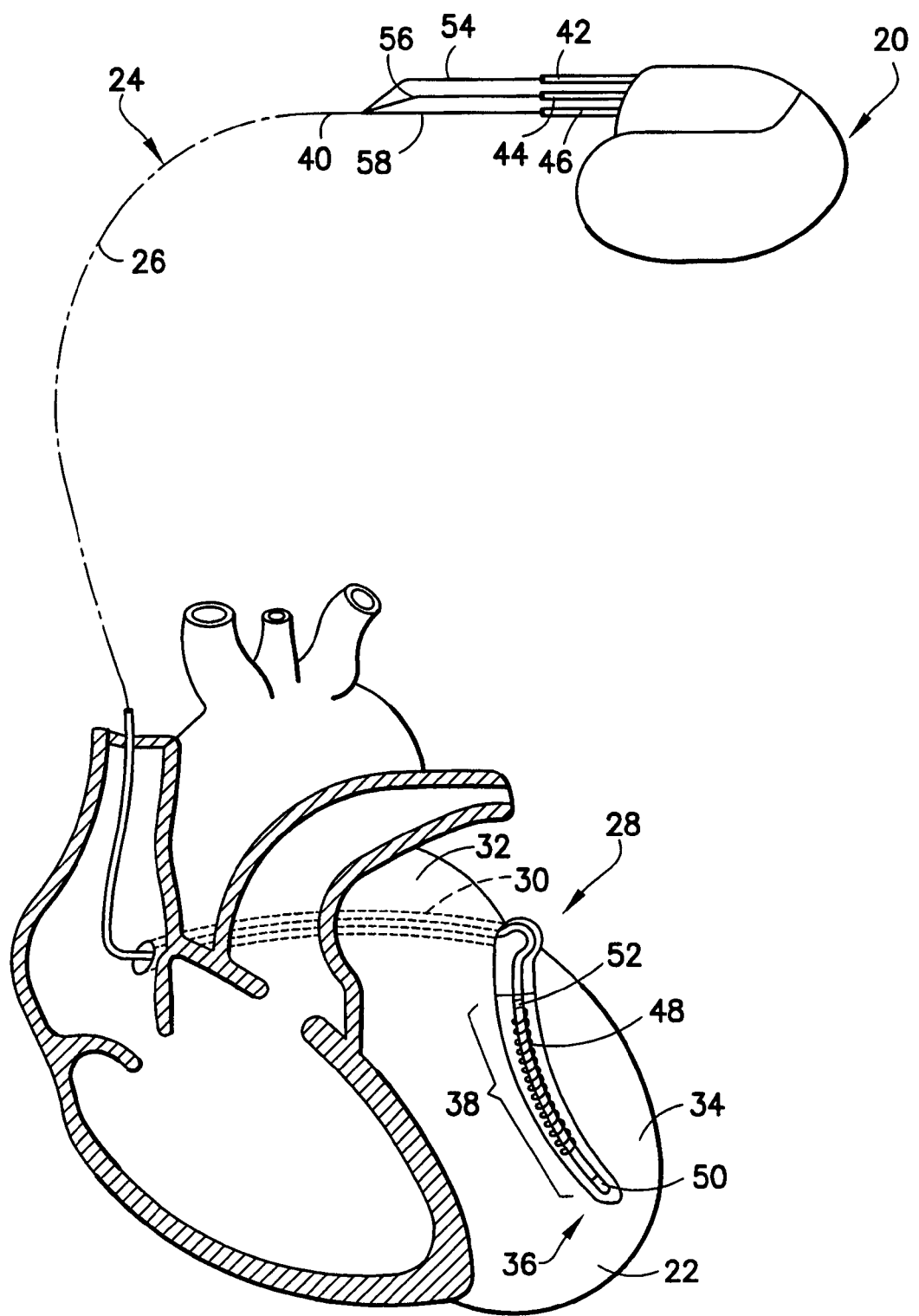
FIG. 1 is a diagrammatic perspective view illustrating an implantable cardiac stimulation device in electrical communication with a patient's heart by a coronary sinus region lead embodying the present invention.

As shown in FIG. 1, a stimulation device 20 is provided in electrical communication with a patient's heart 22 by way of a lead 24 embodying the present invention intended for placement in the coronary sinus region 28. Lead 24 provides both left ventricular pacing and defibrillation therapy. Designed for placement in the coronary sinus region of the heart, the lead 24 extends through the coronary sinus ostium 30 and adjacent to the left atrium 32 and the left ventricle 34. As used herein, the phrase "coronary sinus region" refers to the venous vasculature of the left ventricle, including any portions of the coronary sinus, great cardiac vein, left marginal vein, left posterior ventricular vein, middle cardiac vein, and/or small cardiac vein or any other cardiac vein accessible by the coronary sinus.

As will be noted in FIG. 1, the lead 24 includes an elongated lead body 26 having a distal end 36 which includes an electrode assembly 38 and a proximal end 40 which leads to a plurality of terminals 42, 44, 46 at the proximal end of the lead body, each terminal being connected into the stimulation device 20 which includes a defibrillation electrode, preferably a gold-filled silicone rubber electrode (FIG. 3).

The electrode assembly 38 includes a defibrillation electrode 48 and first and second pacing electrodes 50, 52. The first pacing electrode 50 includes a distal tip or apical electrode at the distal end of the lead which is spaced from the defibrillation electrode and positioned at, or adjacent to, the distal end of the lead body adjacent the apex of the left ventricle 34 of the heart 22. The second pacing electrode 52 includes a ring electrode which is spaced proximally from the defibrillation electrode 48 and adjacent the basal region of the left ventricle of the heart for stimulating the basal region. A plurality of conductors 54, 56, 58 serve to connect each electrode 48, 50, 52, via the respective terminals 42, 44, 46 to the stimulation device 20.

Figure 4:
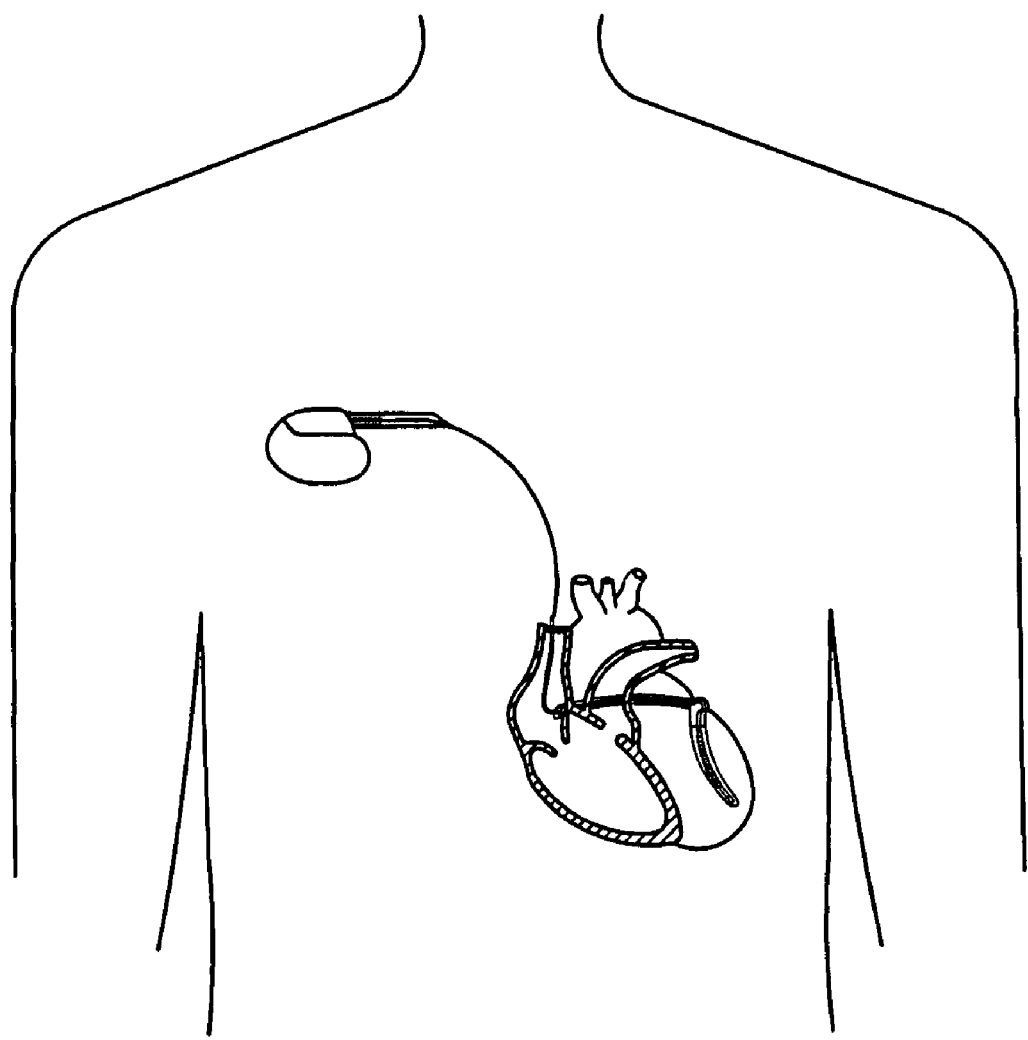
FIG. 4 is a schematic view showing one illustrative embodiment of an implant location for the implantable cardiac stimulation device and lead.

It is noteworthy that no lead is required in the right ventricle, also that stimulation device 20 is preferably mounted in the patient's right side (FIG. 4) in order to define a defibrillation vector that travels through a large portion of the heart, namely between the defibrillation electrode 48 on the left side and stimulation device 20.

FIG. 2 shows the basic design of the lead of the invention. The LV apical pacing and sensing is done between the tip electrode and the defibrillation electrode. The LV basal sensing and pacing is done between the CS ring or pacing electrode 52 and the defibrillation electrode 48. Simultaneous apical and basal pacing is done from the apical pacing tip or pacing electrode 50 to the CS ring electrode 52. Of course, the defibrillation shock is delivered between the patient's right-side implanted stimulation device 20 and the defibrillation electrode. In one embodiment defibrillation electrode 48 is in the form of a metallic coil as illustrated in FIG. 2. In an alternate embodiment, defibrillation electrode 48 is in the form of a conductive polymer electrode, preferably a gold-filled silicone rubber that facilitates passage down through the thin left-sided veins (FIG. 3). Thus, in a preferred design, the defibrillation electrode 48 is thin and flexible so that it will not tend to "catch" as it proceeds through a percutaneous lead introducer or through vasculature, nor become ingrown by fibrotic tissue, chronically, to the extent of a conventional wire-wrapped defibrillation coil electrode, thereby allowing for extraction of the lead.

As thus can be seen from the foregoing, the present invention provides a coronary sinus region implantable lead which provides both ventricular pacing and defibrillation therapy. The defibrillation electrodes and pacing electrodes are positioned to provide efficient pacing and defibrillation therapy from a single lead. This allows for the implanter to achieve complete stimulation therapy while only implanting a single lead in the coronary sinus region.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. An implantable cardiac lead for placement in a coronary sinus region of a heart, the lead comprising:
   a lead body defining a distal end and a proximal end;
   a plurality of terminals at the proximal end of the lead body;
   an electrode assembly comprising a defibrillation electrode and first and second pacing electrodes, the first pacing electrode spaced from the defibrillation electrode and positioned proximate to the distal end of the lead body for placement in electrical contact with an apex of a left ventricle of the heart, the second pacing electrode spaced proximally from the defibrillation electrode for placement in electrical contact with a basal region of the left ventricle of the heart; and
   a plurality of conductors connecting each electrode to a respective one of the terminals at the proximal end of the lead body;
   wherein the first and second pacing electrodes respectively stimulate the apex and basal region simultaneously.

2. The cardiac lead of claim 1
   wherein the first pacing electrode comprises a distal tip electrode proximate to the distal end of the lead body; and
   wherein the second pacing electrode comprises a ring electrode.

3. The cardiac lead of claim 1
   wherein the defibrillation electrode comprises a metallic coil.

4. The cardiac lead of claim 1
   wherein the defibrillation electrode comprises a gold-filled polymer electrode.

5. The cardiac lead of claim 1
   wherein the defibrillation electrode comprises a metal-filled silicone rubber electrode.

6. The cardiac lead of claim 1
   wherein the defibrillation electrode comprises a conductive polymer material.

7. A method of treating congestive heart failure, the method comprising:
   (a) implanting a cardiac lead in a coronary sinus region of a heart, the lead comprising a defibrillation electrode and first and second pacing electrodes, the first pacing electrode spaced from the defibrillation electrode and positioned proximate to the distal end of the lead body and placed in electrical contact with an apex of a left ventricle of the heart, the second pacing electrode spaced proximally from the defibrillation electrode and placed in electrical contact with a basal region of the left ventricle of the heart; and
   (b) simultaneously stimulating the apex and the basal region of the left ventricle from the first and second pacing electrodes.

8. A method of treating congestive heart failure according to claim 7 wherein stimulating the heart comprises:
   (c) stimulating the heart, in one instance, from the first pacing electrode; and
   (d) stimulating the heart, in another instance, from the second pacing electrode.

9. A method of treating congestive heart failure according to claim 8
   wherein a time separation of up to 50 ms exists between the first instance and the second instance.

10. A method of treating congestive heart failure according to claim 7 further comprising:
    (c) providing a defibrillation electrode intermediate the first pacing electrode and the second pacing electrode; and
    (d) stimulating the heart from the defibrillation electrode.

11. A method of treating congestive heart failure according to claim 7
    wherein the first pacing electrode is a distal tip electrode; and
    wherein the second pacing electrode is a ring electrode.

12. A method of treating congestive heart failure according to claim 7
    wherein stimulation of the apex of the left ventricle is performed between the first pacing electrode and the defibrillation electrode; and
    wherein stimulation of the basal region of the left ventricle is performed between the second pacing electrode and the defibrillation electrode.

13. A method of treating congestive heart failure, the method comprising:
    implanting a cardiac lead in a coronary sinus region of a heart, the lead comprising a defibrillation electrode and first and second pacing electrodes, the first pacing electrode spaced distally from the defibrillation electrode and positioned proximate to the distal end of the lead body and placed in electrical contact with an apex of a left ventricle of the heart, the second pacing electrode spaced proximally from the defibrillation electrode and placed in electrical contact with a basal region of the left ventricle;
    implanting an implantable cardiac stimulation device in a right-side location of a patient's body, wherein the implantable cardiac stimulation device comprises a return electrode;
    stimulating the heart from selected ones of the plurality of pacing electrodes; and
    in response to ventricular fibrillation, delivering a defibrillation shock pulse between the defibrillation electrode and the return electrode.

14. A method of treating congestive heart failure according to claim 13 wherein stimulating the heart comprises:
    stimulating the heart, in one instance, from the first pacing electrode; and
    stimulating the heart, in another instance, from the second pacing electrode.

15. A method of treating congestive heart failure according to claim 14
    wherein a time separation of up to 50 ms exists between the first instance and the second instance.

* * * * *